(12) United States Patent
Beltram et al.

(10) Patent No.: US 8,393,356 B2
(45) Date of Patent: Mar. 12, 2013

(54) DEVICE FOR CONTROLLING FLUID MOTION INTO MICRO/NANOCHANNELS BY MEANS OF SURFACE ACOUSTIC WAVES

(75) Inventors: Fabio Beltram, Gorizia (IT); Roberto Cingolani, Genoa (IT); Marco Cecchini, Calci (IT); Salvatore Girardo, Surbo (IT); Dario Pisignano, Lecce (IT)

(73) Assignee: Fondazione Istituto Italiano di Tecnologia, Genoa (IT)

( * ) Notice: Subject to any disclaimer, the term of this patent is extended or adjusted under 35 U.S.C. 154(b) by 349 days.

(21) Appl. No.: 12/670,821

(22) PCT Filed: Jul. 21, 2008

(86) PCT No.: PCT/IB2008/052925
§ 371 (c)(1),
(2), (4) Date: Jan. 26, 2010

(87) PCT Pub. No.: WO2009/013705
PCT Pub. Date: Jan. 29, 2009

(65) Prior Publication Data
US 2010/0200092 A1    Aug. 12, 2010

(30) Foreign Application Priority Data
Jul. 26, 2007  (IT) .............................. TO2007A0554

(51) Int. Cl.
*H02K 44/00*   (2006.01)

(52) U.S. Cl. ......................................... 137/828; 417/50

(58) Field of Classification Search .................. 137/827, 137/828; 310/328; 417/50
See application file for complete search history.

(56) References Cited

U.S. PATENT DOCUMENTS 6,720,710 B1 *  4/2004  Wenzel et al. ............... 310/328
7,942,568 B1 *  5/2011  Branch et al. ............... 366/127

FOREIGN PATENT DOCUMENTS

WO    WO 97/25531     7/1997

OTHER PUBLICATIONS

Kurosawa et al., "Surface acoustic wave atomizer," *Sensors and Actuators A* 50:69-74 (1995).
Renaudin et al., "SAW nanopump for handling droplets in view of biological applications," *Sensors and Actuators B* 113:389-397 (2006).
Sritharan et al., "Acoustic mixing at low Reynold's numbers," *Applied Physics Letters* 88:054102-1-054102-3 (2006).
Wixforth et al., "Acoustic manipulation of small droplets," *Anal Bioanal Chem* 379:982-991 (2004).

* cited by examiner

*Primary Examiner* — Craig Schneider
(74) *Attorney, Agent, or Firm* — Kilpatrick Townsend and Stockton LLP

(57) ABSTRACT

A device for controlling fluid motion in a micro/nanofluidic structure of channels by means of surface acoustic waves is described. The device comprises a structured volume of material bearing a predetermined configuration of micro/nanofluidic channels for holding and transferring amounts of fluids adapted to define at least one fluid inlet and at least one fluid outlet and presenting a hydrophobic behaviour for the fluids to be handled and a substrate made of material with piezoelectric properties coupled to the micro/nanofluidic channels.

15 Claims, 5 Drawing Sheets

DEVICE FOR CONTROLLING FLUID MOTION INTO MICRO/NANOCHANNELS BY MEANS OF SURFACE ACOUSTIC WAVES

CROSS REFERENCES TO RELATED APPLICATIONS

This application is a U.S. National Phase Application under 35 U.S.C. §371 of International Application No. PCT/IB2008/052925, filed on Jul. 21, 2008, which claims the benefit of Italian Application No. TO2007 A000554, filed on Jul. 26, 2007, which is herein incorporated by reference for all purposes.

The present invention relates to active control of the fluid motion in micro/nanofluidic structures on chips, and more specifically it relates to a device for controlling fluid motion in micro/nanochannels.

The micro/nanofluidic systems, that is with a cross-section of the fluid distribution channels comprised between 1 nanometre and 1 millimetre, represent devices which are important for biological, chemical, biochemical, optofluidic and sensing applications, given that they allow to perform many diagnostic experiments, of chemical and optical type, rapidly and in parallel, integrating many complex analytical functions, while limiting the consumption of reagents and samples, given that the volumes of liquid usually employed are comprised between 1 picolitre and a few nanolitres.

In order to obtain a high efficiency and integration of these systems, an active control of the fluid motion through active elements which can be integrated on chips such as pumps, valves and mixers is required.

Unfortunately, a widespread distribution of the micro/nanofluidic devices is strongly limited by the low possibilities to incorporate these elements and ensure an accurate and reproducible control of the fluid motion at the inlet, outlet and along the path of micro/nanofluidic channels.

Other difficulties are due to some basic requirements for devices with practical use: the devices need to be relatively inexpensive, compatible with the fluid analysis processes (for example compatible with electro-osmotic flows, that is non-conductive), portable and compact, and they should have excellent sealing properties among all the elements in a manner such to bear internal or external high pressures.

Typically, polar fluids such as water solutions can fill hydrophilic micro/nanochannels (that is with a contact angle smaller than 90°) by spontaneous capillarity, but this movement cannot be controlled accurately. On the contrary, in case of hydrophobic capillaries or networks of capillaries the same fluids somehow have to be forced into the micro/nanochannels. The pressures required can be generated through external pumping systems such as for example syringe pumps connected to the devices. However, these systems require an ideal sealing and a number of connections to external devices which drastically reduce the portability and the compactness of the entire system.

An alternative known pumping method is based on the electro-osmotic flow control. This allows transporting fluids and it provides an almost constant velocity within the channels and it can be integrated without invasive external connections. However, this approach requires high voltage drops along the channels, amounting to hundreds or thousands of volts, and it is quite sensitive to the properties of the fluid, such as the ionic strength, pH and ionic composition, as well as to the presence of electrical charges on the surface of the channels. Furthermore, the electro-osmotic flow control technique is typically not capable of pumping liquids at high flow rates (greater than 1 mm/s) in any type of micro/nanochannel.

Known are other miniaturised fluid handling devices, which include controlling the fluid motion through electrostatic, piezoelectric, thermopneumatic, electromagnetic, bimettalic means and by means of shape-memory alloys. Most of these devices are made employing microelectromechanical systems (MEMS) technologies on silicon, but the poor reliability, and the high times and costs of production are aspects that limit their distribution.

Recently, studies regarding use of polymer materials, whose processing is now possible due to the latest micro/nanomanufacturing technologies, such as soft lithography and imprint lithography, which allow to generate plastic micro/nanostructures in a quick manner and at a low cost with high performance, have been carried out with the aim of reducing the overall production costs of fluidic micro/nanodevices.

For example, a structure of conventional miniaturised channels can be transferred to a flexible polymer such as the polydimethylsiloxane (PDMS), with the aim of integrating pneumatically-controllable pumps and valves. The advantage of this approach lies in the manufacturing simplicity and inexpensiveness, quick prototyping and the general biocompatibility of the materials. Disadvantageously, the valves and the pumps thus produced are basically passive systems, due to the difficulties encountered when integrating actuator devices, typically operated pneumatically from the external. In particular, these solutions are hardly compatible with an electronic control integrated with a chip bearing a micro/nanofluidic structure in combination with other analysis devices.

A micro-pumping technology worth mentioning is described in WO97/25531. This technology is based on the use an "acoustic streaming flow" mechanism for forcing fluids into capillary pipes. The "acoustic streaming flow" transport technique is based on the transfer of energy and momentum of an acoustic wave to a fluid medium present along the wave propagation path. The interaction determines a net increase of the kinetic energy of the fluid medium and its movement. This phenomenon has been known to scientists since late 1800 and it was recently studied also from the system's quantistic nature point of view. Due to the energy and momentum conservation laws, the "acoustic streaming flow" technique leads to the motion of the fluid medium to which it is applied along a direction matching the direction of propagation of the acoustic wave. Due to the progressive moving of the fluid away from the acoustic source and due to the absorption of the acoustic power by the fluid and the propagation medium, the efficiency of this pumping mechanism decreases along the path of the fluid and practically prevents the creation of long microfluidic channels, without the inclusion of sets of micro-pumps distributed along the length of the channel.

A different type of sensors and actuators applying the "acoustic streaming flow" physical mechanism mentioned beforehand has been recently developed exploiting the characteristics of the surface acoustic waves (SAW).

A surface acoustic wave is typically generated along the surface of a piezoelectric material through metallic interdigitated transducers (IDT). The interdigitated acoustic transducers are periodic structures which consist of a succession of comb-like interposed metal strips (electrodes), connected in an alternating manner to collection tracks for distributing the electrical signal as shown in FIG. 1. The transducer period is determined by the distance between opposite strips of electrodes and it determines the period of the above-mentioned surface acoustic wave. The shape of a transducer may vary depending on the spectral characteristics required by the acoustic wave. The periodicity of the transducer and the velocity of the acoustic wave in the piezoelectric medium determine the resonance frequency for SAW excitation. According to the standard configuration of SAW propagation on a lithium niobate substrate, the resonance frequencies of a transducer are typically of the order of magnitude of tens or hundreds of MHz. Different operation frequencies, i.e. different transducer periodicities, can be employed depending on the typical sizes of the micro/nanofluidic network to which the transducer is coupled.

FIG. 1 shows a typical configuration of an interdigitated transducer for the generation of a surface acoustic wave.

The acoustic wave is generated at the free surface of a piezoelectric substrate with elastic properties by the application of an alternating voltage at the metal electrodes of the transducer. When a radiofrequency voltage is applied across the transducer electrodes, the piezoelectricity properties of the substrate allow the conversion of the electrical signal into a lattice deformation of the substrate material, hence generating a periodic deformation of the free surface of the substrate beneath the transducer, capable of exciting surface acoustic waves which are propagated at the substrate/air interface. Due to the transducer symmetry, two acoustic waves propagated in opposite directions are emitted off the transducer ends. The propagation can be easily made unidirectional by including known reflectors and absorbers in the geometry of the device.

SAWs are also exploited for transporting and moving small amounts (drops) of liquid deposited on free surfaces, along the direction of propagation of the acoustic wave.

This technology also allows the division and mixture of small amounts of fluid, for example for controlling the movement of reagents provided in form of drops on the surfaces having regions with different chemical functions.

This technology was employed to develop efficient micromixers, included in microfluidic systems to improve mixing operations at the low Reynolds number regimes, strongly improving various biochemical reactions.

The object of the present invention is to provide an improved technique for controlling the fluid motion while entering, exiting and along micro/nanofluidic structures, integrated on chips.

According to the invention such object is obtained due to a device for controlling fluid motion in a micro/nanofluidic structure of channels.

In brief, the present invention is based on the principle of controlling the motion of a fluid element by means of surface acoustic waves propagated in a direction opposite with respect to the desired direction of movement of the fluid, and it regards the control of the inlet, outlet and motion of the fluids in micro/nanochannel networks through pumping systems based on counter-propagation of surface acoustic waves generated by interdigitated transducers on piezoelectric materials.

This mechanism differs from the traditional fluid motion induction method by means of an "acoustic streaming flow" technique, and it leads to a much more efficient pumping and handling of fluids in nano/microchannels. Furthermore, this device geometry allows an efficient construction of micropumps and microvalves integrated in the microfluidic systems, therefore providing and effective possibility of assembling and integrating systems.

Herein described are also processes for manufacturing micro/nanofluidic devices on chips, including integrated active elements for a complete control of the fluid flow in micro/nano channels.

A micro/nanofluidic device is made by overlapping two functional layers, respectively a piezoelectric substrate, adapted to support the propagation of surface acoustic waves generated by means of microfabricated interdigitate transducers, and a structured layer made of plastic material, in which a micro/nanochannels network required for the intended application is defined.

It is necessary for the operation of this mechanism that the microfluidic circuit exhibits a hydrophobic behaviour for the fluid to be pumped: in case of hydrophilic channels, fluid propagation and circuit filling happens spontaneously due to capillary forces, and is not effectively controlled by acoustic waves.

When implementing the device on chips, the channel structured layer is aligned with the transducers in such a manner that the digital electrodes of the transducers are arranged in an orthogonal manner with respect to the lateral walls of the channels to which they are associated.

The substrate currently preferred for SAWs excitation is Lithium Niobate ($LiNbO_3$), though other substrates like quartz, $Bi_{12}GeO_{20}$ or $LiTaO_3$ or any other piezoelectric material having sufficient piezoelectric coupling can also possibly be used.

SAW generation is obtained by applying an alternating voltage on the interdigitated transducer electrodes deposited on the piezoelectric substrate surface. In a preferred embodiment, transducers whose configuration comprises an array of pairs of electrodes polarised with an alternating polarity are used.

The transducers are fabricated by means of standard metal film deposition techniques such as electron beam lithography or photolithography, metal evaporation, lift-off to name a few examples.

The surface of the piezoelectric substrate can be coated by a thin film made of inert material, for example silicon oxide, whose thickness is much smaller with respect to the length of the surface acoustic wave, adapted to form a base layer suitable for biological and biochemical applications.

The channel structured layer is preferably fabricated by means of replica molding techniques, that is by preparing an elastomeric replica mold by means of casting the prepolymer liquid of an elastomer against a mold patterned to form a relief structure similar to the model of the desired channel structure. The subsequent thermal curing leads to the transfer of the configuration from the master mold to the elastomeric replica. The same technique can be used to generate polymer replicas using a solution of a thermoplastic polymer in its solvent. Other different techniques and materials can be used to obtain a network of microchannels, including polymers, semiconductors, glasses, ceramics, plastics, etc. Various plastic materials provide an excellent mechanical and thermal stability and high resistance to solvents, acids and bases.

The currently preferred choice of a replica molding technique for implementing polydimethylsiloxane (PDMS) channels offers various advantages:

polydimethylsiloxane, due to its elastic characteristics, can be released easily, also by complex and fragile structures;

polydimethylsiloxane replicas can be typically conformed to the substrate on a relatively large area without chemical treatments of the substrate surface;

polydimethylsiloxane provides a surface with a lower interface free energy (21 6×10$^{-3}$ J/m$^2$) and chemically inert, making the related devices suitable for biological applications;

polydimethylsiloxane exhibits hydrophobic behaviour for most aqueous solutions;

devices can be quickly prototyped, with low production costs.

Conveniently, the final device is assembled by overlapping the channel structured layer on the piezoelectric substrate bearing the transducers and by subsequent sealing (thermally, by photon irradiation, by exposure to plasma, chemically, etc) reversibly or irreversibly for the definition of closed channels.

In order to generate a surface acoustic wave on the substrate, the transducers are connected to an external alternating voltage source through the collector strips of its electrodes.

When the fluidic circuit is hydrophobic, surprisingly the propagation of the surface acoustic waves across the meniscus of the liquid produces a net force on the fluid directed in the opposite direction with respect to the wave propagation direction (Actually this interaction leads to atomization of the liquid, and the microdroplets eventually coalesce in front of the meniscus, i.e. towards the acoustics source). The fluid is thus dragged along the channel towards the source of the acoustic wave.

It is experimentally observed that this effect is more efficient and flexible with respect to the traditional "acoustic streaming flow" technique, which necessarily forces the fluid to move along a direction matching the direction of propagation of the acoustic wave.

Therefore, the configuration proposed does not require the acoustic wave propagation along the entire micro/nanofluidic channel, but a strong interaction is required only at the liquid/air interface facing the incoming acoustic wave. This allows full control of the fluid flow by means of a single transducer for each channel, instead of a series of transducers distributed along the channel as for the conventional "acoustic streaming" configuration. As a matter of fact, the propagation of the acoustic wave from the transducer to the fluid element (drop) to be dragged occurs without a substantial deterioration of the wave and energy drop, and at greater distances, given that the propagation of the surface acoustic wave occurs at the interface between the piezoelectric substrate and the air.

When the surface acoustic wave is turned off, the fluid motion is immediately stopped given that no more energy is transferred to the fluid, which is held within a hydrophobic channel where spontaneous capillarity is suppressed. The flow can be restored at any time by turning on the acoustic wave. It is therefore possible to drag the fluid along the channel in arbitrary steps by simply turning on and off the RF power to the transducer generating the SAW.

For example, according to the described technique it is possible to control a fluid element (a drop) from the inlet to the outlet of a channel 1 mm long, 500 microns wide and 50 microns high in a few seconds.

Furthermore, the filling or travel velocity of fluid along the channel can be controlled by varying the power of the surface acoustic wave, that is the power of the electric signal applied to the interdigitated transducer.

By using the device described according to the invention, it is possible to make micro/nanofluidic devices with active micro-pumps and valves integrated, each determined by a selective configuration of active transducers and hydrophobic channel ducts, which do not require any external actuator element and can be controlled entirely by electronic means. A single transducer can be used as a pump or as a valve to achieve fluid flow control into a single micro/nanochannel, in such a manner to obtain a very small packaging volume and an ideal integration into complex micro/nanofluidic devices.

Further characteristics and advantages of the invention shall be outlined further in detail in the subsequent detailed description, provided for exemplifying and non-limiting purposes, with reference to the attached drawings, wherein.

Any process well known in the art can be used to make the polymer microfluidic circuit, e.g. hot embossing of thermoplastic polymers or replica molding of elastomeric polymers; a preferred choice is replica molding of PDMS, which provides suitably hydrophobic features.

Figure 1:
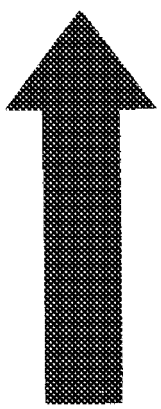
FIG. 1 is an exemplifying representation of a surface acoustic wave generating interdigitated transducer according to the known art.
Figure 1:
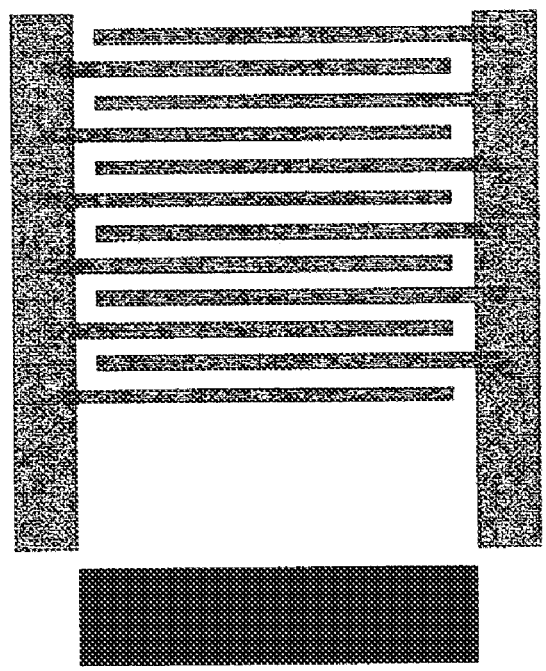
Figure 2:
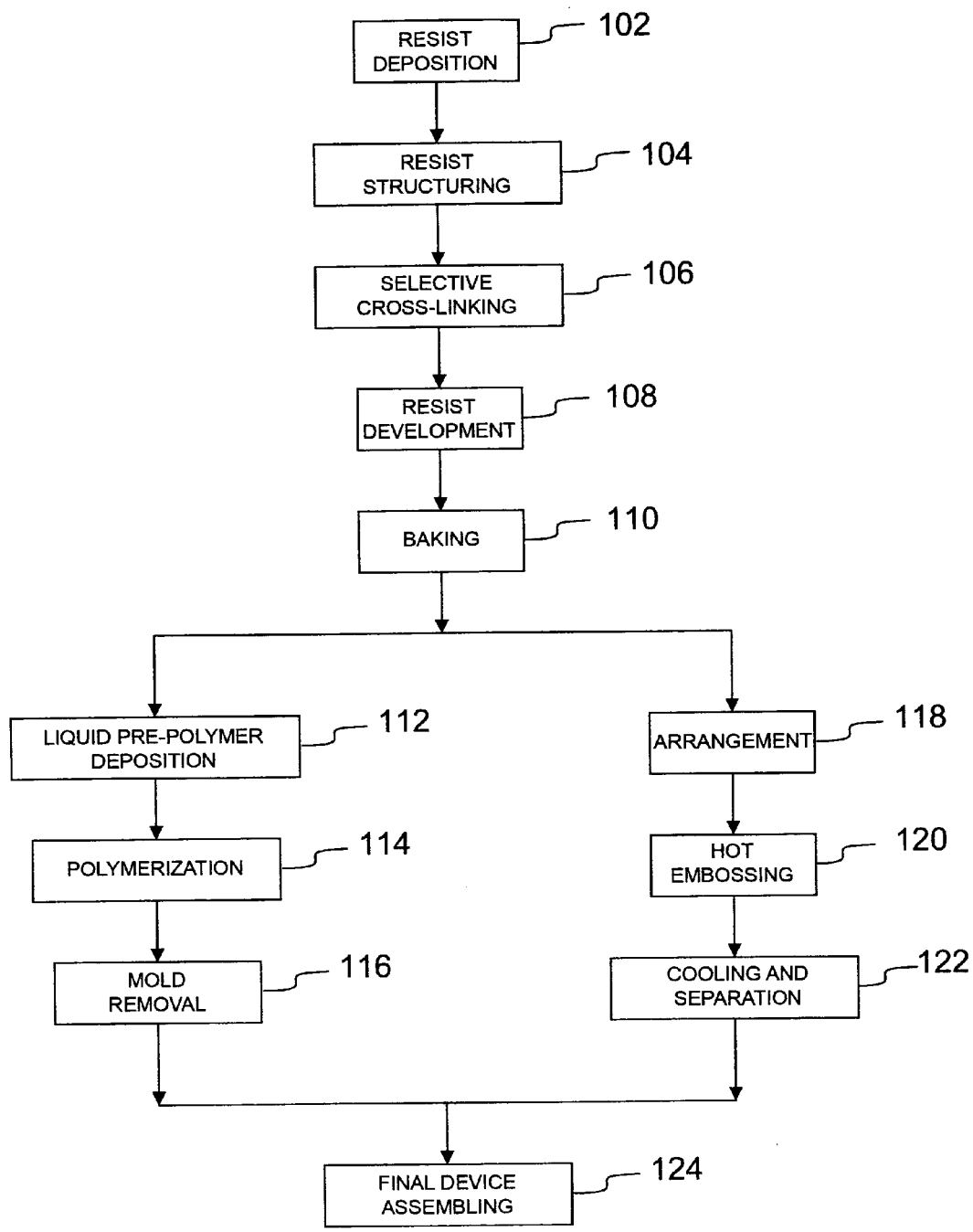
FIG. 2 is a flowchart of an exemplary embodiment of a micro/nanofluidic structure fabrication process according to the invention.

Referring to FIGS. 2 and 3 described hereinafter is a succession of steps for a micro/nanofluidic structure fabrication process.

In a first step 102 a resist is applied onto a substrate 10, for example a silicon substrate.

Figure 3A:
FIGS. 3a-3i are cross-sectional schematic views of the elements which intervene in the micro/nanofluidic structure fabrication process according to the flow chart of FIG. 2.

Preferably, the resist is applied on the substrate by means of a spin coating technique, forming a resist layer 20 having a thickness comprised between a few nanometres and hundreds of microns, at the desired height (depth) of the channel (FIG. 3a).

Figure 3B:
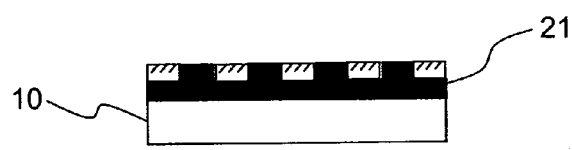

In a subsequent step 104 the resist layer 20 is structured, for example by exposure to radiation by means of an aligning mask, leading to a structured resist layer 21 (FIG. 3b).

Figure 3C:

In a step 106 the layer 21 is baked in order to selectively cross-link the structured portion of the layer itself and in a step 108 the layer is developed in order to produce a patterned resist layer 22 (FIG. 3c).

After a subsequent bake curing process (for example for approximately 15 minutes at a temperature of 180° C.) in a step 110, the layer 22 is ready to be used as the mold master to replicate the master features on thermoplastic or elastomeric materials as shown in FIGS. 3d-3i.

Figure 3D:
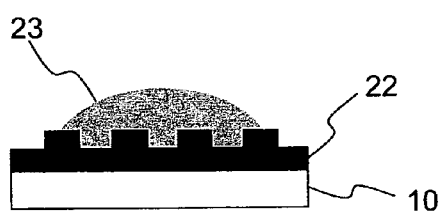

In a step 112 a liquid prepolymer layer 23, is cast on the master fabricated in the previous steps (FIG. 3d). In the subsequent step 114 the prepolymeric fluid is polymerized in situ forming a related layer 24 (FIG. 3e), e.g. by baking at a temperature of 140° C. for 15 minutes, according to standard replica molding processes. In the subsequent step 116 the polymeric mold is peeled off from the master in such a manner to obtain a patterned polymer layer 25 with the negative shape of the master layer 22 (FIG. 3f).

A nano-imprinting or hot-embossing process can be used as an alternative to steps 112-116.

Figure 3G:
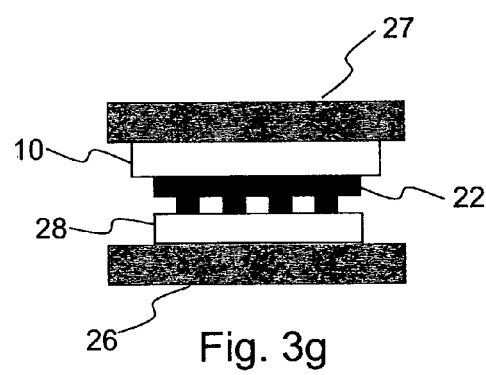
Figure 3E:
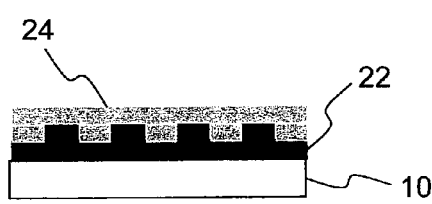

In a step 118 a polymer substrate 28 is inserted into a molding machine, directly in contact with a lower heater layer 26 and with layer 22, then heated to a temperature exceeding the glass transition temperature $T_g$ of the polymer (FIG. 3g).

Figure 3H:
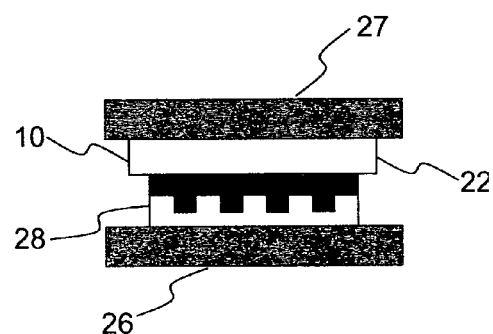
Figure 3F:
Figure 3I:
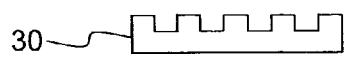

In a subsequent step 120 the layer 22, using an upper heater layer 27, is pressed against the polymer substrate 28 transferring its negative configuration therein (FIG. 3h). After a certain contact time between layer 22 and layer 28, in step 122, the product is cooled to a temperature below $T_g$, then the master is separated from the polymeric substrate. As a result a patterned polymeric layer 30 with the negative shape of the master is obtained as shown in FIG. 3i.

There are categories of polymers (for example, thermoplastic polymers) which can be modelled using both the replica molding techniques (steps 112-116) and the nano-imprinting techniques (steps 118-122) and categories of polymers (for example, elastomers) which can be modelled using only the replica molding technique.

Subsequently, in a step 124 the device is assembled by overlapping the structured layer 25 or 30 bearing the predetermined network of channels on a piezoelectric substrate 31, providing a reversible or irreversible sealing.

Given that the single interdigitated transducers can be used as pumps or valves, different geometries can be exploited successfully to make portable and compact so-called "lab-on-chip".

Figure 4A:
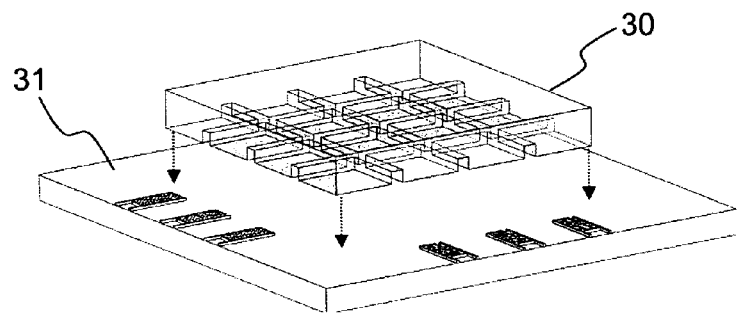
FIGS. 4a and 4b are axonometric representations of a micro/nanofluidic device comprising a complex network of micro/nanochannels and transducers for generating surface acoustic waves according to a device for controlling the fluid motion which is the subject of the invention.
Figure 4B:
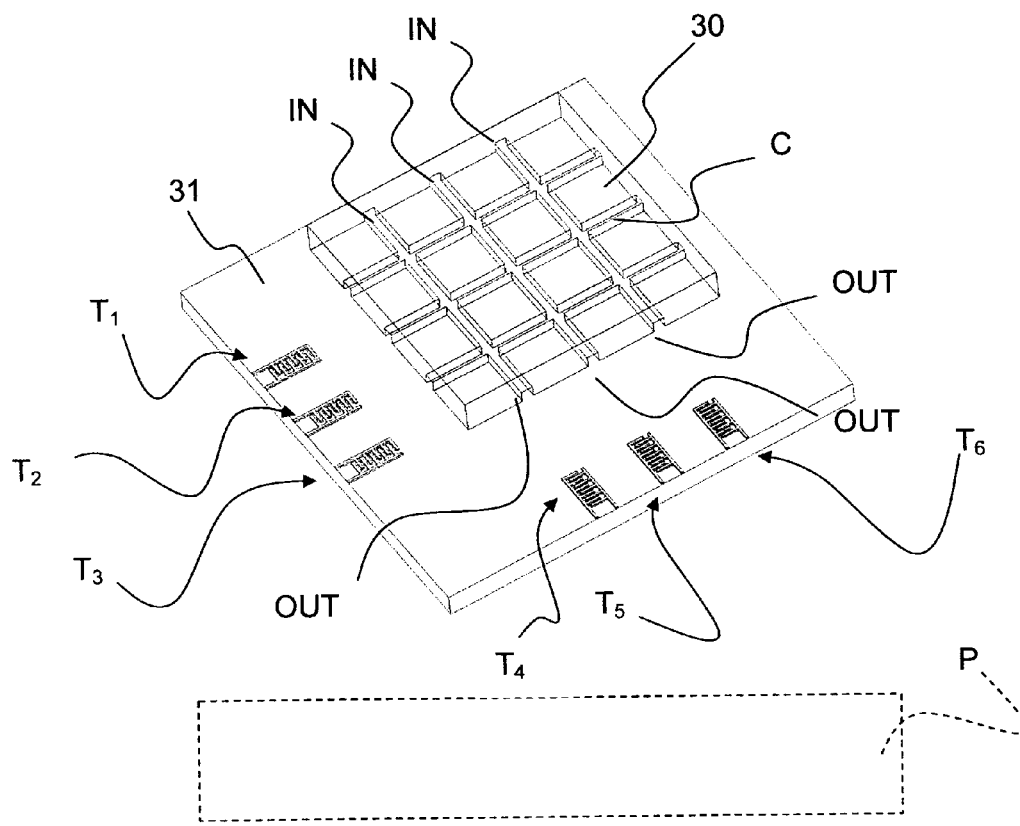

Shown in FIGS. 4a and 4b is an example of a prototype device comprising six transducers $T_1$-$T_6$ deposited on the piezoelectric substrate 31 for controlling the motion of one or more fluid elements in a complex network of micro/nanochannels defined in the structured layer 30. The transducers are connected to an electronic control circuit P, for example a microprocessor unit, provided for their selective activation and the adjustment of the SAWs propagation energy, depending on the desired application.

This configuration allows various operations, such as mixing fluids at the channel crosses or splitting an amount of fluid by simultaneous activation of the transducers associated to different channels when a fluid element is at the cross region of the abovementioned channels. Microchambers could also be added as reaction chambers or reagent products collection chambers.

The arrangement of FIGS. 4a, 4b is a result of an accurate alignment of the substrate surfaces for supporting the active elements (transducers, serving as pumps and valves) and the structured layer which defines the micro/nanochannels and possible reservoirs. Such alignment can for example be provided with the help of microscopes or specific instruments for aligning two surfaces (for example, mask-aligners).

Elastomeric materials are suitable to generate polymeric stamps incorporating micro/nanochannels and reliably ensuring a good conformal contact with different surfaces, therefore a good sealing of the assembled devices. Other polymer materials can be used to coat substrate 31, as long as they ensure a good sealing with surface, thermal, optical or chemical bonding techniques between layer 31 and substrate 30. Such bonding process can be reversible if the stamp used is made of elastomeric materials, or irreversible if based on chemical, optical or thermal treatments.

To obtain such reliable bonding between the abovementioned layers and preserve the characteristics of the transducers, deposition of thin films of polymeric or ceramic materials on the piezoelectric surface may also be required.

Figure 4C:
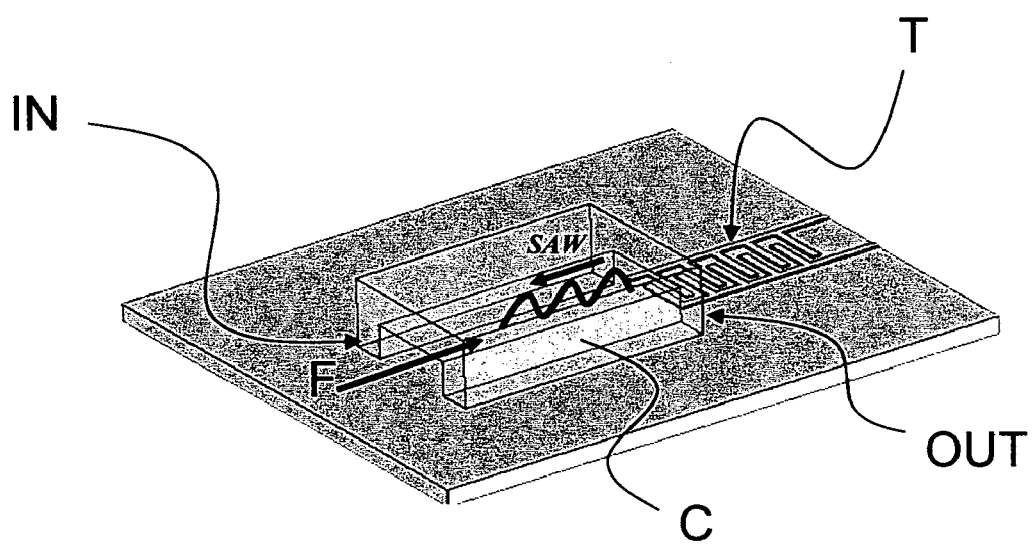
FIG. 4c is an exemplifying representation of a fluid motion control configuration according to the invention.

In the structure illustrated in FIGS. 4a, 4b fluid elements such as drops or the like can be controlled accurately and dragged form one or more inlets IN to one or more outlets OUT along the micro/nanochannels C. As better indicated in FIG. 4c, the motion of a fluid element occurs towards the direction indicated by arrow F and it is controlled by a surface acoustic wave SAW which propagates towards the opposite direction, generated by an interdigitated transducer T arranged in proximity to the channel outlet OUT.

Specifically, the fluid motion along the channels can be interrupted with immediate effect by interrupting the radiofrequency supply to one or more corresponding transducers associated to the generation of the surface acoustic waves, and the travel velocity of the fluid can be controlled by modifying the power of the signal applied to the transducers.

For example, an interdigitated transducer formed by 20 pairs of electrodes with a periodicity of 24 microns and an aperture of 500 microns, deposited on the lithium niobate substrate, can drag a drop of water in 1.3 seconds into a microchannel made of PDMS 500 microns wide, 50 microns high and 1 mm long, with moderate power supplied to the transducer (20 dBM). A drop of water can be completely dragged from the inlet IN to the outlet OUT of the microchannel C within 2 seconds. Furthermore, the fluid motion can be quickly stopped by "turning off" the surface acoustic wave.

Advantageously, the interdigitated transducers can also be used for localising the position of a fluid element according to the known art of analysing SAW echo signals.

Therefore, the method described offers a straightforward and efficient process for providing micro/nanofluidic devices with integrated active pumps and valves thus improving micro/nanofluidic devices in terms of performances for industrial application.

Conveniently, the micro/nanochannels can be fabricated with different materials to obtain monolithic or hybrid channel structures, for example made of ceramic, glass, inorganic or organic semiconductor, or polymer materials, provided that the surface of the channels is hydrophobic, either intrinsically or after performing a suitable processing step.

A device as shown in FIG. 4b can be used as a dispensing device for controlling the fluid volume at the outlet or inlet of micro/nanochannels or for dragging a fluid drop from the inlet to the outlet of one or more micro/nanochannels. This allows a quick transport of a small volume of fluid (from a few millilitres to a few picolitres) in different regions of a chip through dragging along one or more micro/nanochannels connected or not connected to a network.

The fluid can be a liquid, a molten polymer or a polymer solution, a solution containing nanoparticles, organic molecules, inorganic molecules or their blends, a solution containing biological molecules, provided that it is non-wetting for the fluidic circuit surface.

A microstructured device subject of the invention can be used to control biochemical reactions, genomic and proteomic reactions and complex analysis systems, for example for chemical or biochemical applications in which solvent-resistant, acid and/or base resistant, heat-resistant or chemically inert materials with hydrophobic behaviour are required. Furthermore, it can be used for biological applications in which the materials used must have a specific gas permeability, or be materials capable of preventing the adsorption of molecules and their unfolding at the surfaces. This is a typical characteristic of hydrophobic materials.

Further applications provided for are optofluidic applications, including fabrication of laser devices, LED light-emitting devices, polarisers, filters, and waveguides.

Obviously, subject to the principle of the invention, the implementations and details of embodiment may widely vary with respect to the points argued and illustrated solely for exemplifying and non-limiting purposes, without for this reason departing from the scope of protection of the present invention as defined by the attached claims.

The invention claimed is:

1. A device for controlling fluid motion in a micro/nanofluidic structure of channels, the device comprising:
   a structured volume of material, bearing a predetermined configuration of micro/nanofluidic channels for holding and transferring amounts of fluids, said channels adapted to define at least one fluid inlet and at least one fluid outlet, and
   a substrate made of material with piezoelectric properties, said substrate coupled to said configuration of micro/ nanofluidic channels, bearing means for active control of the motion of an amount of fluid including transducer means, said transducer means comprising at least one pair of interdigitated electrodes applied on said substrate, said electrodes arranged to selectively generate a surface acoustic wave adapted to propagate on the substrate and interact with said amount of fluid; wherein the device is further characterised in that the channels are hydrophobic for the fluids to be controlled, and in that said transducer means are arranged in proximity to a fluid outlet of said configuration of channels in such a manner to generate a surface acoustic wave propagating from the fluid outlet to a fluid inlet of the configuration, whereby the motion of said amount of fluid is induced towards the direction opposite to the surface acoustic wave propagation direction, due to the interaction between the surface acoustic wave and the meniscus of the non-wetting fluid facing said surface acoustic wave.

2. The device according to claim 1, comprising an electronic circuit for controlling said transducer means, arranged for adjusting the intensity of the electrical signal at the electrodes, in such a manner to control the power of the excited surface acoustic waves and adjust the travel velocity of the fluid along the channel.

3. The device according to claim 1, wherein said channels are configured in a volume of hydrophobic material.

4. The device according to claim 1, wherein said structured volume bearing the channels is fabricated using nano-imprinting or hot-embossing techniques applied to a polymer material.

5. The device according to claim 1, wherein the piezoelectric substrate surface is coated with a thin film made of inert material, whose thickness is substantially smaller with respect to the length of the surface acoustic wave, adapted to form a base layer suitable for biological or biochemical applications.

6. A chip comprising a device for controlling fluid motion in a micro/nanofluidic structure of channels, according to claim 1.

7. The device according to claim 1, wherein said transducer means are arranged to generate surface acoustic waves whose propagation wavelength is smaller with respect to the characteristic dimension of the fluid channel.

8. The device according to claim 7, wherein said transducer means are arranged in proximity to said fluid outlet directed in such a manner to have interposed interdigitated electrodes extending orthogonally with respect to the direction of development of the walls defining the channels.

9. The device according to claim 1, wherein said structured volume bearing the channels is fabricated using replica molding techniques applied to a polymer material.

10. The device according to claim 9, wherein said material is polydimethylsiloxane (PDMS).

11. The device according to claim 1, comprising an electronic circuit for controlling said transducer means, arranged for selective activation of a plurality of transducer devices associated to different channels to control the excitation of surface acoustic waves separately to induce the motion of the amount of fluid in the different channels.

12. The device according to claim 11, wherein said electronic control circuit is arranged to induce the motion of an amount of fluid in confluent channels, to determine the mixture of fluids in the cross region of the channels.

13. The device according to claim 11, wherein said electronic control circuit is arranged to induce the motion of an amount of fluid in diverging channels for splitting an amount of fluid from the intersection region of channels.

14. The device according to claim 11, wherein said electronic control circuit is arranged to induce the motion of an amount of fluid from reagent collection chambers and/or towards reaction chambers, provided in said structured volume of material.

15. The device according to claim 11, wherein said electronic control circuit is arranged to localise the position of a fluid element in the channel through techniques for analysing the echo signals of a surface acoustic wave.

* * * * *